United States Patent
Kittlaus et al.

(10) Patent No.: US 10,451,592 B2
(45) Date of Patent: Oct. 22, 2019

(54) ARRANGEMENT OF HILIC CHROMATOGRAPHY COLUMN AND SPE ENRICHMENT ARRANGEMENT FOR PREPARING SAMPLES AND ANALYZING PESTICIDES

(71) Applicant: joint analytical systems GmbH, Moers (DE)

(72) Inventors: Stefan Kittlaus, Dresden (DE); Jorg Radtke, Neukirchen-Vluyn (DE)

(73) Assignee: Joint Analytical Systems GmbH, Moers (DE)

( * ) Notice: Subject to any disclaimer, the term of this patent is extended or adjusted under 35 U.S.C. 154(b) by 476 days.

(21) Appl. No.: 13/754,655

(22) Filed: Jan. 30, 2013

(65) Prior Publication Data

US 2013/0140238 A1     Jun. 6, 2013

Related U.S. Application Data

(63) Continuation-in-part of application No. PCT/EP2011/058145, filed on May 19, 2011.

(30) Foreign Application Priority Data

Jul. 30, 2010 (DE) .................. 10 2010 036 770

(51) Int. Cl.
*G01N 30/46* (2006.01)
*G01N 30/20* (2006.01)
(Continued)

(52) U.S. Cl.
CPC ........... *G01N 30/461* (2013.01); *G01N 1/405* (2013.01); *G01N 30/06* (2013.01); *G01N 30/08* (2013.01);
(Continued)

(58) Field of Classification Search
CPC ................ B01D 15/18; B01D 15/1864; B01D 15/1885; B01D 15/1807; B01D 15/203;
(Continued)

(56) References Cited

U.S. PATENT DOCUMENTS 4,446,105 A * 5/1984 Dinsmore et al. .............. 422/70
5,242,586 A * 9/1993 Ransohoff .................. 210/198.2
(Continued)

OTHER PUBLICATIONS

Wang et al. Novel, fully automatic hydrophilic interaction/reversed-phase column-switching high-performance liquid chromatographic system for the complementary analysis of polar and apolar compounds in complex samples. Journal of Chromatography A, 1204 (2008) 28-34.*

(Continued)

*Primary Examiner* — Katherine Zalasky
(74) *Attorney, Agent, or Firm* — Thorpe North and Western, LLP

(57) ABSTRACT

An arrangement for preparing samples and analyzing pesticides in samples contains an HILIC chromatography column with a first pump for a predominately low-water and/or non-polar solvent; and SPE enrichment arrangement; a second chromatography column with a second pump for a predominantly water-rich and/or polar solvent; a detector; and a valve arrangement for controlling the stream of sample and matrix, which valve arrangement is designed in such a way that the sample stream, in a first switching state of the valve arrangement, can be conducted from the HILIC chromatography column to the SPE enrichment arrangement and, in a second switching state, the sample enriched in the SPE enrichment arrangement can be conducted in the opposite direction from the SPE enrichment arrangement through the second chromatography column to the detector.

9 Claims, 2 Drawing Sheets

(51) Int. Cl.
  *G01N 30/40* (2006.01)
  *G01N 1/40* (2006.01)
  *G01N 30/06* (2006.01)
  *G01N 30/08* (2006.01)

(52) U.S. Cl.
  CPC ............ *G01N 30/20* (2013.01); *G01N 30/40* (2013.01); *G01N 30/46* (2013.01); *G01N 30/462* (2013.01); *G01N 1/4044* (2013.01); *G01N 2030/085* (2013.01)

(58) Field of Classification Search
  CPC ...... B01D 15/30; B01D 15/305; B01D 15/32; B01D 15/325; B01D 15/424; B01D 15/426; G01N 30/02; G01N 30/38; G01N 30/40; G01N 30/461; G01N 30/462; G01N 30/463; G01N 30/465; G01N 30/468; G01N 2030/027; G01N 2030/402; G01N 2030/405; G01N 2030/407; G01N 2030/388; G01N 2030/382; G01N 2030/385
  See application file for complete search history.

(56) References Cited

U.S. PATENT DOCUMENTS

| | | | | |
|---|---|---|---|---|
| 5,522,988 | A * | 6/1996 | Cortes et al. | 210/198.2 |
| 6,074,555 | A * | 6/2000 | Boos et al. | 210/198.2 |
| 6,402,947 | B1 * | 6/2002 | Altamirano et al. | 210/198.2 |
| 6,426,006 | B1 * | 7/2002 | Zambias et al. | 506/12 |
| 6,485,648 | B1 * | 11/2002 | Gjerde et al. | 210/635 |
| 6,541,273 | B1 * | 4/2003 | Plaisance | 436/178 |
| 6,641,783 | B1 * | 11/2003 | Pidgeon | G01N 30/20 210/656 |
| 7,862,716 | B2 * | 1/2011 | Zelechonok et al. | 210/198.2 |
| 2001/0035372 | A1 * | 11/2001 | Bouvier et al. | 210/198.2 |
| 2002/0121468 | A1 * | 9/2002 | Fischer et al. | 210/198.2 |
| 2002/0185442 | A1 * | 12/2002 | Maiefski et al. | 210/656 |
| 2004/0188333 | A1 * | 9/2004 | Allington et al. | 210/198.2 |
| 2006/0231471 | A1 * | 10/2006 | Ohkura | 210/198.2 |
| 2008/0093300 | A1 * | 4/2008 | Clarke et al. | 210/656 |
| 2008/0164211 | A1 * | 7/2008 | Lindner et al. | 210/656 |
| 2008/0236256 | A1 * | 10/2008 | Brand | G01N 30/08 73/61.55 |
| 2009/0090856 | A1 | 4/2009 | Grant et al. | |
| 2010/0024527 | A1 | 2/2010 | LaMarr et al. | |

OTHER PUBLICATIONS

Hennion; "Solid-phase extraction: method development, sorbents, and coupling with liquid chromatography"; Journal of Chromatography, 1999 Published by Elsevier Science B.V.

Anastassiades, et al.; "Validation of a Simple and Rapid Multiresidue Method (QuEChERS) and its Implementation in routine Pesticide Analysis"; MGPR, May 2003, Aix en Provence, France.

Ingelse, et al.; "Determination of polar organophosphorus pesticides in aqueous samples by direct injection using liquid chromatography—tandem mass spectrometry"; Journal of Chromatography; 2001 Elsevier Science B.V.

Wilson, et al.; "2D LC Separation and Determination of Bradykinin in Rat Muscle Tissue Dialysate with On-Line SPE-HILIC-SPE-RP-MS"; Chromatographia 2007; 66, October (No. 7/8).

Sanchez et al., "Automated determination of folate catabolites in human biofluids (urine, breast milk and serum) by on-line SPE-HILIC-MS/MS"; Journal of Chromatography; 2010 Elsevier B.V.

* cited by examiner

ARRANGEMENT OF HILIC CHROMATOGRAPHY COLUMN AND SPE ENRICHMENT ARRANGEMENT FOR PREPARING SAMPLES AND ANALYZING PESTICIDES

RELATED APPLICATIONS

This application is a continuation-in-part of International Application PCT/EP2011/058145 filed May 19, 2011, and which specified the United States, and which is based on and claims priority to German Application DE 10 2010 036 770.2 filed Jul. 30, 2010, both of which are hereby incorporated by reference.

TECHNICAL FIELD

The invention relates to an assembly for sample preparation and the analysis of pesticides in samples by means of chromatography. Pesticides are used to protect plants against pest or vermin. As they may enter the food chain in the form of residues, legal thresholds are set which are controlled by analysis. The analysis of pesticides is carried out for different samples in different sample matrices. Therefore, it is an object of the analysis to separate the pesticides in the samples as well as possible from the matrix and carry out the analysis afterwards. It is an ongoing object of the development to achieve a high accuracy, to automatize the sample preparation and analysis and to reduce the workload and the consumption of chemicals for the analysis.

PRIOR ART

The publication "Validation of a Simple and Rapid Multiresidue Method (QuEChERS) and its Implementation in Routine Pesticide Analysis" by M. Anastassiades, E. Scherbaum and D. Bertsch, Poster on the MGPR Symposium, May 2003 in Aix en Provence, France, discloses a simplified method for sample preparation for the instrumental analysis of pesticides by means of GC-MSD or LC-MS. The method replaces various steps by simpler steps. Various chemicals, such as $MgSO_4$, NaCl and Acetonitril are added and different preparation steps are carried out, such as shaking or centrifugation are carried out for the sample preparation.

The multi-method known as "S19" for determining residues of plant protective agent in food by Specht comprises essentially the extraction and distribution, gel permeation chromatography (GPC), chromatography with a small silica gel column and the subsequent gas chromatographic detection with various detectors.

According to the ChemElut method by Alder the homogenized sample is extracted with methanol after adjusting a unitary water content and the centrifugalized extract is cleaned afterwards by liquid-liquid distribution at diatom earth. Thereby, pesticides which shall be analyzed can be separated from interfering matrix components. The relatively large amount of dichloromethane required for elution is reduced afterwards and the remains taken with a solvent which is suitable for the measurement, usually methanol.

All known methods provide automation by copying method steps which are usually carried out manually. The sample is extracted with different solvents. Cleaning and measuring the extract requires many steps in the laboratory (liquid-liquid distribution, SPE, GPC, . . . ).

In order to simplify the time consuming sample preparation there are powerful detectors available. The automation is effected similar to above mentioned prior art.

The high work load and the high material consumption is disadvantageous with all known methods. The accuracy of the results and the number of pesticides which can be analyzed is limited with some of the methods.

DISCLOSURE OF THE INVENTION

It is an object of the invention to make the sample preparation more economic and to reduce the work load and the material consumption. According to the present invention this object is achieved with an assembly comprising:

(a) a Hydrophilic Liquid Interaction Chromatography (HILIC) chromatography column with a first pump for a solvent which is essentially non-polar and/or has a low water content;
(b) a Solid Phase Extraction (SPE) accumulation assembly;
(c) a second chromatography column with a second pump for a solvent which is essentially polar and/or has a high water content;
(d) a detector; and
(e) a valve assembly for controlling the sample and matrix flow formed in such a way that the sample flow is led in a first switching position of the valve assembly from the HILIC chromatography column to the SPE accumulation assembly and wherein in a second switching position the sample accumulated in the SPE accumulation assembly is led in the opposite direction from the SPE accumulation assembly through the second chromatography column to the detector.

In a preferred modification of the invention the solvent which is essentially polar and/or has a high water content is flushed in the first switching position of the valve assembly in opposite direction through the second chromatography column and disposed of afterwards.

The assembly according to the present invention enables the full automation of the sample preparation and analysis. The raw extracts are directly cleaned, i.e. an interfering matrix is removed, and analyzed. The extraction of the sample is effected before sampling with a solvent which is non-polar and/or has a low water content. Acetonitril (ACN) is particularly suitable. A mixing ratio of 95 Vol.-% ACN and 5 Vol.-% water has been proven to be particularly advantageous. The extract can be directly used for the measurement. The cleaning of the extract is performed and automated by chromatography in the HILIC chromatography column.

The use of a HILIC column is particularly advantageous because pesticides can be well separated from the interfering matrix components. The pesticides elute earlier than the matrix and caught by the SPE accumulation assembly. The matrix remains in the HILIC chromatography column and can be eluted at a later stage.

It can be seen that contrary to previous attempts for automation no existing method is imitated but a new method is applied with a new assembly. Instead of carrying out a liquid-liquid distribution a HILIC chromatography column is used. While the pesticides are analyzed in the second step in the second, analytic chromatography column, the HILIC chromatography column may be cleaned.

Preferably the second, analytical chromatography column is operated as a reverse-phase (RP)-chromatography column. Surprisingly, it was found that coupling a HILIC chromatography column with an RP chromatography column provides particularly reproducible results with good detection limits and sensitivities for pesticide methods.

The assembly according to the invention enables the detection of the spectrum of active components of known classical methods without manual sample preparation. The accumulation in the SPE accumulation assembly has the further advantage that large injection volumina may be applied. Thereby, detection limits and sensitivity are further increased.

The accumulated components are transferred to the second, analytical column with beginning gradients with the back flush method. Simultaneously, the matrix is eluted from the HILIC chromatography column and the column is conditioned for the next analysis. Disposables are not required for cleaning. This protects the environment and makes the method and the assembly particularly economic.

A preferred embodiment of the invention uses a solvent having a high water content and/or being polar of the pump which comprises at least 90 Vol.-% water at the beginning of the analysis. Furthermore, the solvent having a high water content and/or being polar of the pump may comprise 3 to 10 Vol.-%, preferably 5 Vol.-% Acetonitril and/or MeOH. With such a solvent the accumulated pesticides are flowed from the SPE accumulation assembly to the second, analytical chromatography column according to the back flush-method.

The second chromatography column may be a High Performance Liquid (HPLC) column. It may, however, also be a Gas chromatography (GC) column. The elution is then carried out off-line in the SPE accumulation assembly. The elute is analyzed in the GC column. In other words: the HILIC chromatography column and the SPE accumulation assembly serve as a sample preparation for a GC column. With such a use the accumulated sample from the SPE accumulation assembly is flushed into a container with a solvent, such as ethyl acetate and/or acetone and analyzed with a GC column.

In a particularly preferred modification of the invention a portion of the sample flow which flows in the first switching position through the SPE accumulation assembly during a selected accumulation time is directly led to the detector. They are, in particular, polar pesticides which cannot be accumulated. They are directly flowed to the detector and measured. Simultaneously, the matrix is separated. A mass spectrometer is particularly suitable as a detector.

The described assembly can be operated particularly well with the following steps:
(a) application of a sample resolved in a solvent which is essentially non-polar and/or has a low water content to a HILIC chromatography column with a solvent which is essentially non-polar and/or has a low water content;
(b) accumulating at least a major portion of the pesticides comprised in the sample in an SPE accumulation assembly;
(c) flowing the sample portion with pesticides accumulated in the SPE accumulation assembly in the opposite direction from the SPE accumulation assembly through the second chromatography column with a solvent which is essentially polar and/or has a high water content by switching of a valve assembly after a selected accumulation period; and
(d) detecting the sample portions separated in the second chromatography column.

A portion of the sample flow flowing through the SPE accumulation assembly during a selected accumulation period is preferably directly detected.

The method is particularly advantageous if the HILIC chromatography column is regenerated during a portion of the analysis period in the second switching position with the pump of a mass spectrometer and a pesticide sample portion for gas chromatography is generated with the column during the remaining analysis period.

Further modifications of the invention are subject matter of the subclaims. A preferred embodiment is described below in greater detail with reference to the accompanying drawings.

DESCRIPTION OF THE EMBODIMENT

Figure 1:
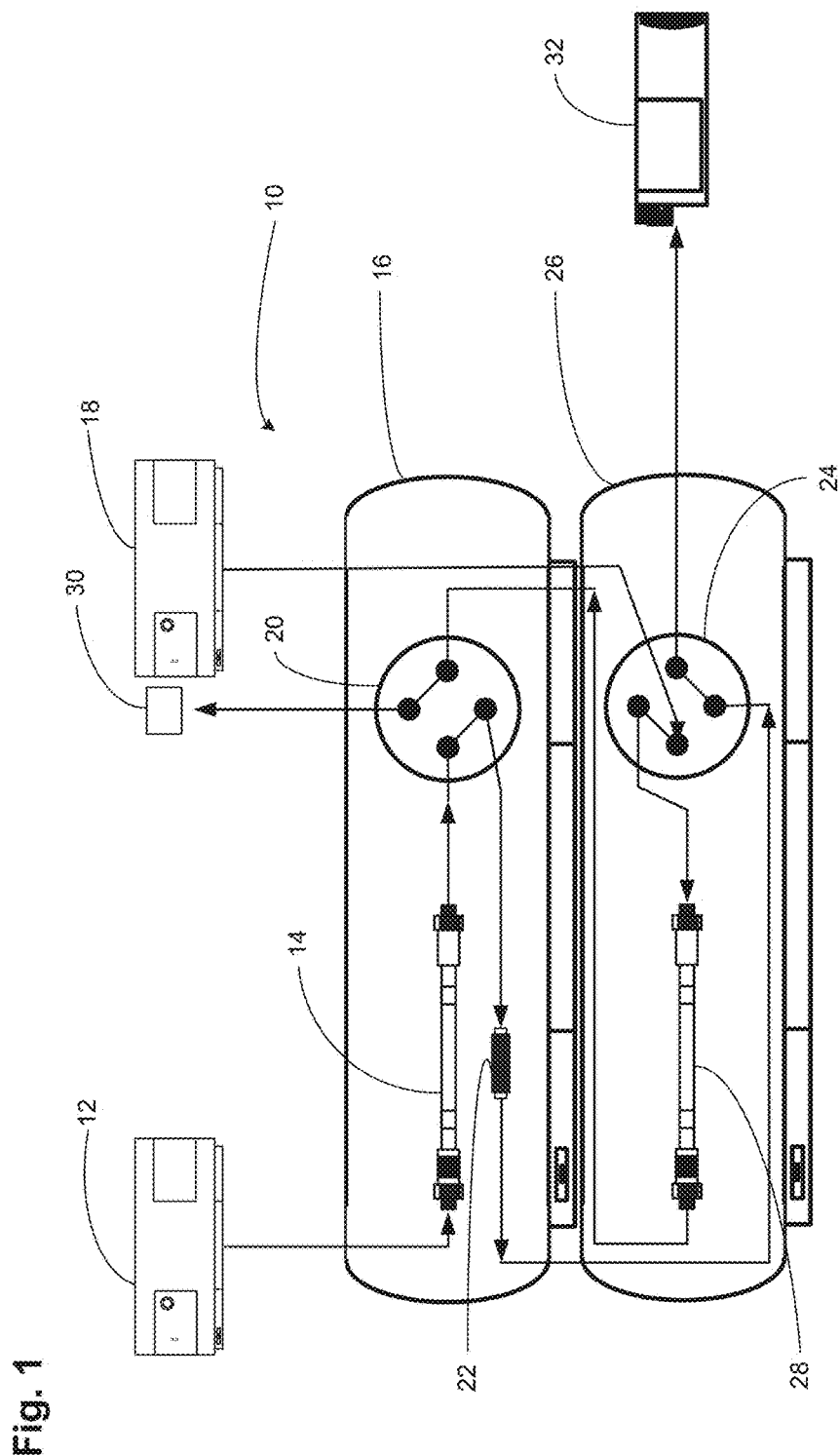
FIG. 1 is a schematic view of an assembly for sample preparation and analysis of pesticides in a first switching position.
Figure 2:
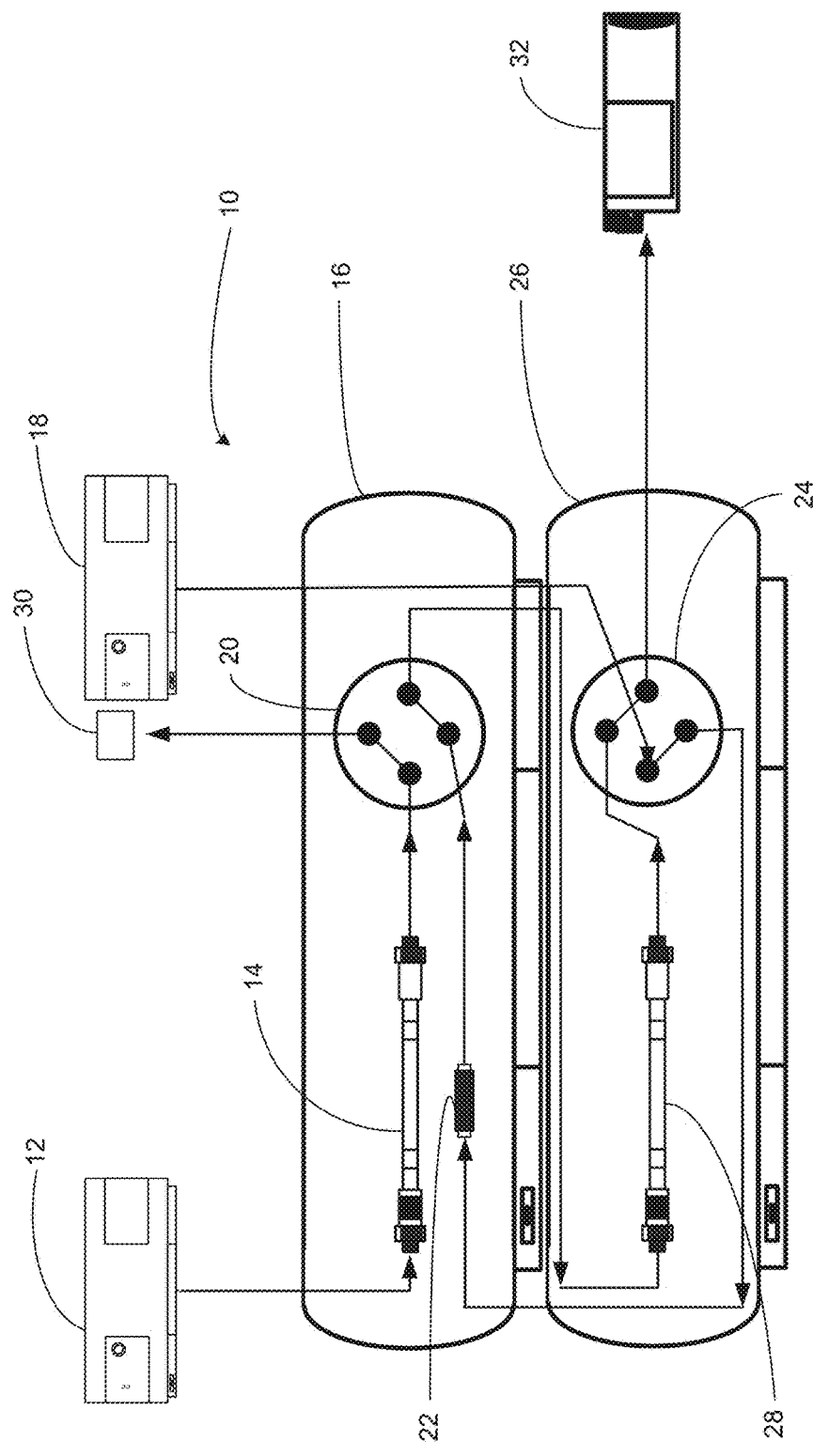
FIG. 2 shows the assembly of FIG. 1 in a second switching position.

FIGS. 1 and 2 show an assembly for the automatic analysis of pesticides in samples, which is generally denoted with numeral 10. The assembly comprises a gradient pump 12, which pumps a solvent initially consisting of 5 vol.-% water and 95 vol.-% ACN to a HILIC chromatography column 14 in an oven 16. The assembly comprises another gradient pump 18 which pumps a solvent initially consisting of 5 vol.-% ACN and/or MeOH and 95 vol.-% water to a valve 20.

In the switching position shown in FIG. 1 the outlet of the HILIC chromatography column 14 is connected to an SPE accumulation assembly 22 through a valve 20. The SPE accumulation assembly of the present embodiment is a short C8 column. By adding water before the SPE accumulation column (not shown) the polarity of the elute can be increased in order to accumulate the pesticides.

The outlet of the SPE accumulation assembly is connected to the sample volume of a LC-MS detector 32 through another valve 24 in an oven 26. An RP-HPLC-column (C18 column) 28 is provided in the oven 26. In the switching position shown in FIG. 1 the solvent flow from the pump 18 flows to HPLC column 28 through the valve 24. The outlet of the HPLC column 28 is connected to waste 30 through the valve 20.

FIG. 2 shows the same assembly as FIG. 1. Valves 20 and 24, however, are switched to a different position. The solvent is flowing through the HILIC column 14 through the valve 20 to the waste 30 by means of the gradient pump 12. Thereby, the HILIC column is cleaned and prepared for the next analysis.

The solvent having a high water content is flowed by the gradient pump 18 through the valve 24 to the SPE accumulation assembly 22. It then flows in the opposite direction as in FIG. 1 through the SPE accumulation assembly 22 to the valve 20. The valve 20 is switched to a position where the sample with the pesticides flows through the valve 20 to the HPLC column 28 for analyzing. The outlet of the HPLC column 28 is connected to the LC-MS detector 32 through valve 24.

The assembly operates as follows:
The method starts with the injection of 5 microliters of the untreated extract solution. In the first switching position of the valves 20 and 24 the sample (raw extract) with the pesticides which shall be analyzed dissolved in ACN and water at a ratio of 95:5 is flowed through the HILIC chromatography column 14 by means of the pump 12. The pesticides are there separated from the main part of the irrelevant, interfering matrix. The matrix mainly remains in the HILIC chromatography column 14. A large portion of the pesticides elute early after about 1 to 4 minutes. Large portions of the matrix are still present in the HILIC column at that stage. The remaining sample portion flows to the SPE accumulation assembly 22. There, the pesticides accumulate. A small portion of the pesticides, in particular low molecular, polar pesticides, will not remain in the SPE accumulation assembly 22 but flow through the SPE accumulation assembly 22 during this accumulation period (FIG. 1) directly to the detector 32. They are, thereby, detected already in this switching position.

After about 4 minutes the matrix in the HILIC is sufficiently separated from the pesticides which shall be analyzed. Valves 20 and 24 are then switched in such a way that the situation of FIG. 2 is obtained. In this switching position the pesticides accumulated in the SPE accumulation assembly are flowed in the opposite direction from the SPE accumulation assembly 22 to the HPLC column 28 with the solvent having a high water content with 95 vol-% water and 5 vol.-% ACN. Gradient pump 18 elutes the components from the SPE accumulation assembly according to the inverted stream principle to the analytical HPLC column. The pesticides which are essentially freed of the matrix are separated therein and detected by the detector 32. This is effected by the gradient used for separation on the HPLC column 28. Starting with a high water content the elution power is slowly increased by increasing the content of Methanol and/or ACN. Simultaneously, the HILIC chromatography column 14 is regenerated or cleaned with the gradient pump 12.

In another embodiment, which is not shown, GC analysis is performed instead of flowing the sample which is separated from the matrix to a HPLC column. The sample is then at first flushed into a separate container by the SPE accumulation assembly. The such prepared sample can be analyzed in a known manner by means of gas chromatography.

The invention claimed is:

1. A method for sample preparation and the analysis of pesticides in samples, comprising the steps of:
   application of a sample of interfering matrix containing raw extracts resolved in a first solvent to a Hydrophilic Liquid Interaction Chromatography (HILIC) chromatography column with said first solvent;
   accumulating at least a major portion of pesticides comprised in said sample in a Solid Phase Extraction (SPE) accumulation assembly in a first switching position and leading a portion of said sample which flows in said first switching position through said SPE accumulation assembly during a selected accumulation period directly to a mass spectrometer;
   flowing said major portion of pesticides accumulated in said SPE accumulation assembly in the opposite direction from said SPE accumulation assembly through a second chromatography column with a second solvent, the second solvent having a larger polarity and/or a higher water content than the first solvent by switching a valve assembly after said selected accumulation period from said first switching position to a second switching position; and
   detecting sample portions separated in said second chromatography column.

2. A method according to claim 1, additionally including the step of directly detecting by said mass spectrometer the sample flow flowing directly to the mass spectrometer through the SPE accumulation assembly during said selected accumulation period.

3. A method according to claim 1, additionally including the step of regenerating and/or cleaning the HILIC chromatography column after switching said valve assembly to said second switching position thereby eluting said HILIC chromatography column and conditioning said HILIC chromatography column simultaneously with transferring the said major portion of pesticides accumulated in said SPE accumulation assembly to the second chromatography column.

4. A method according to claim 1, wherein the first solvent initially comprises at least 90 Vol.-% acetonitrile (ACN).

5. A method according to claim 1, wherein the first solvent initially comprises 0 to 10 Vol. % water.

6. A method according to claim 1, wherein the second solvent comprises at least 90 Vol.-% water.

7. A method according to claim 1, wherein the second solvent comprises 3 to 10 Vol. % acetonitrile and/or MeOH.

8. A method according to claim 1, wherein the first solvent initially comprises 5 Vol.-% water.

9. A method according to claim 1, wherein the second solvent comprises 5 Vol.-% acetonitrile and/or MeOH.

* * * * *